United States Patent [19]

Shell

[11] Patent Number: 4,975,428

[45] Date of Patent: Dec. 4, 1990

[54] TREATMENT OF GLAUCOMA USING PHOSPHODIESTERASE INHIBITORS

[75] Inventor: John W. Shell, Hillsborough, Calif.

[73] Assignee: Iolab Corporation, Claremont, Calif.

[21] Appl. No.: 200,809

[22] Filed: May 31, 1988

[51] Int. Cl.$^5$ ........................................... A61K 31/535
[52] U.S. Cl. ................................................. 514/230.5
[58] Field of Search ...................................... 514/230.5

[56] References Cited

U.S. PATENT DOCUMENTS

| | | | |
|---|---|---|---|
| 3,978,213 | 8/1976 | Lapinet et al. | 424/180 |
| 4,490,374 | 12/1984 | Bandurco et al. | 424/251 |
| 4,721,784 | 1/1988 | Combs | 544/105 |
| 4,753,945 | 6/1988 | Gilbard et al. | 514/263 |

OTHER PUBLICATIONS

Association for Research in Vision and Ophthalmology Annual Meeting Abstract, vol. 29, 1988 (mailed 3/18/88).
Arch. Int. Physiol. Biochem., Nov. 1984, 92(4): S69-79.
W. S. Hillis and M. Been European Heart Journal (1982)3, Supplement D), 97-101.

*Primary Examiner*—Douglas W. Robinson
*Assistant Examiner*—Zohreh A. Fay
*Attorney, Agent, or Firm*—Benjamin F. Lambert

[57] ABSTRACT

Lowering of intraocular pressure, e.g. in the treatment of glaucoma is carried out by administering a phosphodiesterase inhibitor to a patient. Particular ophthalmic pharmaceutical compositions are disclosed for topical application to the eye.

7 Claims, No Drawings

TREATMENT OF GLAUCOMA USING PHOSPHODIESTERASE INHIBITORS

BACKGROUND OF THE INVENTION

In the sympathetic nervous system cascade, adenosine triphosphate (ATP) is converted by action of a catecholamine, such as epinephrine, to cyclic adenosine monophosphate (cAMP) which is then converted to 5'-adenosine nomophosphate (5'-AMP) by the action of the enzyme phosphodiesterase (PDE). This cascade results in physiological responses to environmental stresses, the so-called adrenergic effects.

PDE inhibitors include papaverine and the xanthines such as theophylline and caffeine. PDE inhibitors are used in cosmetics as set forth in U.S. Pat. No. 3,978,213. Theophylline as well as other PDE ingibitors are used as a bronchodilator for relief of the symptoms of asthma.

Glaucoma is an ocular disorder most often characterized by increased intraocular pressure which, over time, may cause impaired vision or blindness. Treatments include topical agents such as pilocarpine (a cholinomimetic drug); timolol maleate (a β-adrenergic receptor blocking agent); epinephrine (an α- and β-adrenergic receptor agonist); dipivefrin (a prodrug of epinephrine) and demecarium bromide (a cholineesterase inhibitor).

Systemic agents used to treat glaucoma include carbonic anhydrase inhibitors such as acetazolamide.

An object of the present invention is an effective treatment for glaucoma by providing an agent which lowers intraocular pressure.

SUMMARY OF THE INVENTION

A treatment for lowering intraocular pressure is provided whereby a phosphodiesterase inhibitor is administered to a patient.

DETAILED DESCRIPTION OF THE INVENTION

Particular PDE inhibitors include compounds of the following formula (I):

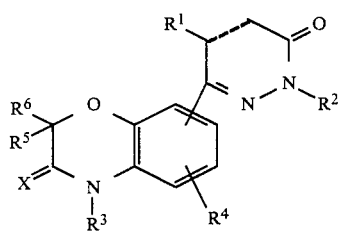

wherein
X may be H and H or O;
$R^1$ may be H, $C_{1-6}$alkyl, $C_{3-6}$branched-chain alkyl or $C_{3-6}$cycloalkyl;
$R^2$ may be H, $C_{1-6}$alkyl, $C_{3-6}$branched-chain alkyl, $C_{3-6}$cycloalkyl or $C_{2-6}$alkenyl;
$R^3$ may be H, $C_{1-6}$alkyl, $C_{3-6}$branched-chain alkyl or $C_{3-6}$cycloalkyl, and when X is 2H, $R^3$ may also be acyl, arylacyl or alkanesulfonyl;
$R^4$ may be H, halogen, $C_{1-6}$alkyl, $C_{3-6}$branched-chain alkyl, $C_{3-6}$cycloalkyl or $C_{1-6}$alkoxy;
$R^5$ and $R^6$ may each be H, $C_{1-6}$alkyl, $C_{3-6}$branched-chain alkyl or $C_{3-6}$cycloalkyl; and the dotted line may be a single or double bond between C4 and C5 of the pyridazine ring.

Preferred compounds of formula (I) are those wherein $R^1$ is $CH_3$, $R^2$ and $R^3$ are hydrogen, $R^4$, $R^5$ and $R^6$ are hydrogen or $CH_3$, X is O and the pyridazinone ring is attached at C-7 of the benzoxazine ring. A particular compound of formula (I) is 6-[3,4-dihydro-3-oxo-1,4[2H]-benzoxazine-7-yl]-2,3,4,5-tetrahydro-5-methyl-pyridazin-3-one known as ORF 22,867 and having the following formula (Ia):

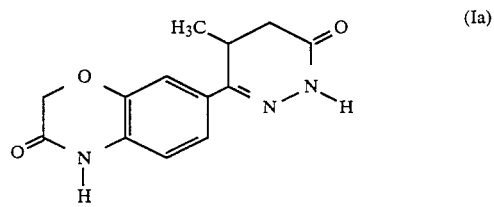

The above compounds of formula (I) are described in U.S. Pat. No. 4,721,784 to Donald W. Combs, issued Jan. 26, 1988 which is hereby incorporated by reference with respect to synthesis and definition of the compounds.

A second particular group of PDE inhibitors to be used in the present invention are quinazolinones of the following formula (II):

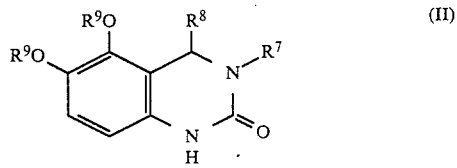

wherein
$R^7$ is hydrogen provided that $R^7$ is hydrogen only when the dotted line linkage represents a saturated bond;
$R^8$ is hydrogen, lower alkyl, cycloalkyl having 4–8 carbon atoms, cycloalkylalkyl wherein the cycloalkyl group has 4–8 carbon atoms and the alkyl group has 1–3 carbon atoms, haloalkyl having 1–3 halogen atoms and 1–4 carbon atoms, norbornyl and norbornylmethyl;
$R^9$ is lower alkyl,
and the dotted line linkage represents a saturated bond or a double bond.

A preferred compound of formula (II) is 5,6-dimethoxy-4-methyl-2[1H]-quinazolinone known as ORF 16,600 or bemarinone and having the following formula (IIa):

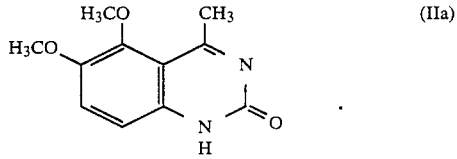

The above compounds of formula (II) are described in U.S. Pat. No. 4,490,374 to Victor T. Bandurco et al. issued Dec. 25, 1984 which is hereby incorporated by reference with respect to synthesis and definition of the compounds.

Other specific PDE inhibitors to be used in the present invention include those described by el Allaf in Arch. Int. Physiol. Biochim., November 1984, 92(4) S 69–79 and by W. S. Hillis in Eur. Heart, J., December 1982, 3 Suppl D, 97–101, including carbazeran.

Systemic formulations of PDE inhibitors are prepared as known in the art, e.g. as set forth in U.S. Pat. No. 4,721,784.

For topical application, the PDE inhibitor may be formulated by preparing a solution or suspension which may be preserved with a preservative such as benzalkonium chloride and formulated with aids such as polyvinyl alcohol or methyl cellulose. The PDE inhibitor may be used in an amount of 0.05 to 2.0% by weight of the ophthalmic composition. The suspension formulation may be similar to that of Dexacidin made by Iolab Pharmaceuticals of Claremont, California with 6 mg/mL hydropropylmethylcellulose, 8.5 mg/mL sodium chloride, 0.5 mg/mL of Polysorbate 20 and 0.04 mg/mL benzalkonium chloride with water q.s. and HCl to adjust the pH to 5.3 to 5.7. Solubility may be enhanced by formulation with a nonionic or anionic surfactant, particularly a nonionic surfactant, such as Pluronic F-68 or by complexation with a cyclodextrin.

Drug delivery systems for use in the present invention include eye drops, ointments and controlled release systems such as Ocusert system from Alza Corporation of Palo Alto, Calif. and those described in my co-pending application, U.S. Ser. No. 61,591, filed June 15, 1987, which is equivalent to EPO Publication No. 251,680, published Feb. 24, 1988.

The dosage to be used will depend on the severity of the patient's condition, the potency of the particular PDE inhibitor and the formulation used. For example, a potent PDE inhibitor may be used at a high dose with, however, a controlled release system as described above. PDE inhibitory activity may be determined in vitro in accordance with the method of W. J. Thompson, et al., in *Adv. Cycli. Nucleotide Res.* Ed. G. Brooker, et al., Vol. 10, pp. 69–92 (1979). This assay measures the ability of compounds to inhibit cyclic nucleotide phosphodiesterase. This enzyme converts either cyclic AMP or cyclic GMP to the noncyclized AMP or GMP, respectively. Compounds are tested at various concentrations in the presence of cyclic AMP (0.10–1.0 $\mu$M containing 0.2 $\mu$Ci $^3$H-cyclic AMP), enzyme, and 0.05 M Tris-Cl buffer (pH 7.4, containing 5 mM $MgCl_2$). After a specified time, the reaction is stopped by heating to 100° C. for one minute. After cooling, 0.10 ml of a solution containing snake venom (1 mg/ml) is added and the reaction is allowed to proceed for 30 minutes. Termination of this reaction is accomplished by the addition of 1.0 ml of 33% Dowex slurry to separate the product from unconverted substrate. An aliquot is removed from the supernatant and quantitated by liquid scintillation spectrometry. The results are expressed as the $IC_{50}$ which is the concentration ($\mu$M) of compound required to inhibit 50% of the cyclic nucleotide phosphodiesterase activity.

In vivo lowering of intraocular pressure may be tested by the method of Goldmann Aplanation Tonometry, Schiotz Tonometry or other systems such as the Tono-Pen or the pneumotonometer.

EXAMPLE 1

To test PDE inhibitors as agents for lowering intraocular pressure, normotensive and hypertensive rabbits were used. Active agents were formulated by preparing a sterile suspension of the agent at a 2% by weight concentration in aqueous saline. Each preparation was coded and tested in conjunction with a placebo which is randomly applied to the normotensive eye. In the hypertensive rabbit, only one eye will be used. Intraocular pressure is determined by either the Tono-Pen handheld tonometer made by Intermedics Intraocular of Pasadena, Calif. a pneumotonometer with topical anesthetic. Data is analyzed with the paired T-test.

Using the above procedure, ORF 16,600 test results were as shown below in Table I:

TABLE I

| Hr | Drug | Placebo | Delta | p |
|----|------|---------|-------|-----|
| 0 | 20.3 ± 2.5 | 20.0 ± 2.9 | +0.3 | .39 |
| 1 | 17.0 ± 2.8 | 17.8 ± 2.3 | −0.8 | .08 |
| 2 | 17.1 ± 3.3 | 17.2 ± 2.0 | −0.1 | .86 |
| 3 | 19.7 ± 2.7 | 20.0 ± 2.6 | −0.3 | .47 |
| 4 | 20.3 ± 3.1 | 20.5 ± 1.8 | −0.2 | .79 |

The relatively weak potency of ORF 16,600 reflected in Table I appears to be caused by a lack of solubility may be enhanced by increasing the solubility of the drug, e.g. by complexing with a $\beta$-cyclodextrin or a poloxomer.

What is claimed is:

1. A method of lowering intraocular pressure in a mammal which comprises administering to the eye a therapeutically effective amount of a phosphodiesterase inhibitor of the formula (I):

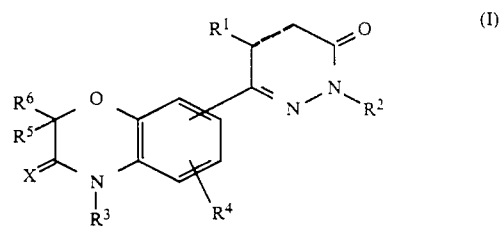

X may be H and H or O;

$R^1$ may be H, $C_{1-6}$alkyl, $C_{3-6}$branched-chain alkyl or $C_{3-6}$cycloalkyl;

$R^2$ may be H, $C_{1-6}$alkyl, $C_{3-6}$branched-chain alkyl, $C_{3-6}$cycloalkyl or $C_{2-6}$alkenyl;

$R^3$ may be H, $C_{1-6}$alkyl, $C_{3-6}$branched-chain alkyl or $C_{3-6}$cycloalkyl, and when X is 2H, $R^3$ may also be acyl, arylacyl or alkanesulfonyl;

$R^4$ may be H, halogen, $C_{1-6}$alkyl, $C_{3-6}$branched-chain alkyl, $C_{3-6}$cycloalkyl or $C_{1-6}$alkoxy;

$R^5$ and $R^6$ may each be H, $C_{1-6}$alkyl, $C_{3-6}$branched-chain alkyl or $C_{3-6}$cycloalkyl; and the dotted line may be a single or double bond between C4 and C5 of the pyridazine ring.

2. The method of claim 1, wherein said administration is topical to the eye.

3. The method of claim 1, wherein said compound is of the following formula (Ia):

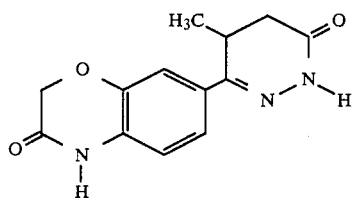 (Ia)

4. The method of claim 1, wherein said pharmaceutical composition comprises the phosphodiesterase inhibitor and a cyclodextrin.

5. The method of claim 1, wherein said pharmaceutical composition comprises the phosphodiesterase inhibitor and a surfactant.

6. The method of claim 5, wherein said surfactant is an nonionic surfactant.

7. The method of claim 1, wherein said pharmaceutical composition is a composition which releases the phosphodiesterase inhibitor in a controlled manner.

* * * * *